(12) United States Patent
Lee et al.

(10) Patent No.: US 9,138,178 B2
(45) Date of Patent: Sep. 22, 2015

(54) METHOD AND SYSTEM FOR SELF-MANAGED SOUND ENHANCEMENT

(75) Inventors: Pui Tong Paul Lee, Hong Kong (CN); Ka Kui Cheng, Tseung Kwan O (CN); Ka Keung John Sung, Kowloon (CN); Ka Cheong Terence Wong, Ma On Shan (CN); Charles Andrew Van Hasselt, Tai Po (CN); Tan Lee, Sha Tin (CN); Chi Shan Anna Kam, Hong Kong (CN)

(73) Assignee: ACE COMMUNICATIONS LIMITED, Hong Kong Sar (CN)

( * ) Notice: Subject to any disclaimer, the term of this patent is extended or adjusted under 35 U.S.C. 154(b) by 811 days.

(21) Appl. No.: 13/184,776

(22) Filed: Jul. 18, 2011

(65) Prior Publication Data

US 2012/0189130 A1 Jul. 26, 2012

Related U.S. Application Data

(60) Provisional application No. 61/371,068, filed on Aug. 5, 2010, provisional application No. 61/379,237, filed on Sep. 1, 2010.

(51) Int. Cl.
*H04R 25/00* (2006.01)
*A61B 5/12* (2006.01)

(52) U.S. Cl.
CPC .................. *A61B 5/128* (2013.01); *A61B 5/121* (2013.01); *H04R 25/75* (2013.01); *H04R 25/70* (2013.01); *H04R 2225/41* (2013.01)

(58) Field of Classification Search
CPC ........ H04R 25/70; H04R 25/75; H04R 25/30; H04R 25/505; H04R 2225/41; H04R 25/558; H04R 2225/39; H04R 2225/55; A61B 5/121; A61B 5/128

USPC .............. 381/56, 58, 60, 312, 314, 315, 317, 381/320, 321, 71.6, 98; 600/559, 25; 73/585

See application file for complete search history.

(56) References Cited

U.S. PATENT DOCUMENTS 4,284,847 A 8/1981 Besserman
4,425,481 A * 1/1984 Mansgold et al. ............ 381/317

(Continued)

FOREIGN PATENT DOCUMENTS

CN 1589588 3/2005
CN 1663528 A 9/2005

(Continued)

OTHER PUBLICATIONS

International Search Report and Written Opinion of PCT Application No. PCT/CN2011/077987, mailed Nov. 10, 2011, 14 pages.

(Continued)

*Primary Examiner* — Huyen D Le
(74) *Attorney, Agent, or Firm* — Hinshaw & Culbertson LLP

(57) ABSTRACT

A system and method are provided for capturing hearing characteristics from self-administered hearing tests or from professionally administered hearing tests, including loudness tolerance levels as at different sound frequencies, as an individualized audiological profile for automatically enhancing audio to complement and address as closely as possible an individual's hearing deficits. The user may self-administer a hearing test on a convenient personal apparatus, such as a smartphone. The system includes the ability for capturing an environment profile. The user's hearing is protected against harm in the enhanced audio setting while being provided with the option of a "enhanced hearing" experience. The invention is useful for any individual seeking an enhanced hearing experience, whether having hearing within normal range or hearing that is impaired. Thus the system is useful as a hearing aid.

23 Claims, 15 Drawing Sheets

(56) References Cited

U.S. PATENT DOCUMENTS

| | | | |
|---|---|---|---|
| 4,879,749 | A | 11/1989 | Levitt et al. |
| 5,944,672 | A | 8/1999 | Kim et al. |
| 6,610,019 | B2 | 8/2003 | Choy |
| 6,944,474 | B2 | 9/2005 | Rader et al. |
| 7,190,795 | B2 | 3/2007 | Simon |
| 7,529,545 | B2 | 5/2009 | Rader et al. |
| 7,613,314 | B2 | 11/2009 | Camp, Jr. |
| 2002/0040254 | A1 | 4/2002 | Neoh |
| 2003/0182000 | A1 | 9/2003 | Muesch et al. |
| 2004/0006283 | A1 | 1/2004 | Harrison et al. |
| 2004/0152998 | A1 | 8/2004 | Stott et al. |
| 2005/0033193 | A1 | 2/2005 | Wasden et al. |
| 2005/0094822 | A1* | 5/2005 | Swartz ............................ 381/56 |
| 2005/0192514 | A1 | 9/2005 | Kearby et al. |
| 2005/0260985 | A1 | 11/2005 | Rader et al. |
| 2006/0094981 | A1 | 5/2006 | Camp |
| 2006/0167335 | A1* | 7/2006 | Park et al. ........................ 600/25 |
| 2006/0215844 | A1 | 9/2006 | Voss |
| 2008/0056518 | A1 | 3/2008 | Burrows et al. |
| 2010/0119093 | A1 | 5/2010 | Uzuanis et al. |
| 2011/0144779 | A1 | 6/2011 | Janse et al. |

FOREIGN PATENT DOCUMENTS

| | | |
|---|---|---|
| CN | 1798452 | 7/2006 |
| CN | 101621729 | 1/2010 |
| CN | 102111699 | 6/2011 |
| WO | 01/24462 A1 | 4/2001 |
| WO | 01/24576 A1 | 4/2001 |
| WO | 03/099113 A1 | 12/2003 |
| WO | 2006/136174 A2 | 12/2006 |
| WO | 2008/011396 A2 | 1/2008 |
| WO | 2012/016527 A1 | 2/2012 |

OTHER PUBLICATIONS

Apple Inc. website, "Hearing-Check for iPhone 3GS, iPhone 4, iPhone 4S, iPhone 5, iPod touch (3rd generation), iPod touch (4th generation), iPod touch (5th generation) and iPad on the iTunes App Store" retrieved from the Internet at https://itunes.apple.com/gb/app/hearing-check/id485312957?mt=8 on Apr. 26, 2013, 3 pages.

Ginger Labs website, "Products, soundAMP", retrieved from the Internet at http://www.gingerlabs.com/cont/soundamp/php on Apr. 19, 2013, 3 pages.

Davis, Adrian, "Epidemiology of hearing disorders", In: Kerr AG, editor. Scott Brown's Otolaryngology, 6th ed., Boston: Butterworth-Heineman, 1997, pp. 2/3/1-2/3/38.

Agrawal, Yuri et al., "Prevalence of hearing loss and differences by demographic characteristics among US adults: data from the National Health and Nutrition Examination Survey, 1999-2004", Archives of Internal Medicine, vol. 168, No. 14 (2008), pp. 1522-1530.

Davis, Adrian, "The prevalence of hearing impairment and reported hearing disability among adults in Great Britain", International Journal of Epidemiology, vol. 18, No. 4 (1989), pp. 911-917.

Quaranta, A. et al., "Epidemiology of hearing problems among adults in Italy", Scandinavian Audiology, Supplement 42, (1996), pp. 9-13.

McFadden, Dennis, Tinnitus: Facts, Theories, and Treatments, National Academy Press, Washington, D.C., 1982, 162 pages.

Nondahl, David M., et al., "Prevalence and 5-year incidence of tinnitus among older adults: the epidemiology of hearing loss study", Journal of the American Academy of Audiology, vol. 13, No. 6, (2002), pp. 323-331.

Sindhusake, Doungkamol et al., "Prevalence and characteristics of tinnitus in older adults: the Blue Mountains Hearing Study", International Journal of Audiology, vol. 42, No. 5, (2003), pp. 289-294.

Tyler, Richard S. et al., "Difficulties Experienced by Tinnitus Sufferers", Journal of Speech and Hearing Disorders, vol. 48, No. 2, (1983), pp. 150-154.

Dobie, Robert A., "Overview: Suffering from Tinnitus", In: Snow J.B., Tinnitus: Theory and Management, 2004, BC Decker Inc., pp. 1-7.

Jastreboff, Margaret M., "Sound therapies for tinnitus management", Progress in Brain Research, vol. 166, (2007), pp. 435-440.

Pleis, John R. et al., "Summary Health Statistics for U.S. Adults: National Health Interview Survey, 2008", National Center for Health Statistics, Vital and Health Statistics, Series 10, No. 242, 2009, 167 pages.

Bexelius, Christin et al, "Evaluation of an Internet-Based Hearing Test—Comparison with Established Methods for Detection of Hearing Loss", Journal of Medical Internet Research, vol. 10, No. 4, (2008), 15 pages.

Henry, James A. et al., "Reliability of computer-automated hearing thresholds in cochlear-impaired listeners using ER-4B Canal Phone earphones", Journal of Rehabilitation Research and Development, vol. 40, No. 3, (2003), pp. 253-264.

Henry, James A. et al., "Reliability of hearing thresholds: Computer-automated testing with ER-4B Canal Phone earphones", Journal of Rehabilitation Research and Development, vol. 38, No. 5, (2001) pp. 567-581.

Margolis, Robert H. et al., "Qualind: A Method for Assessing the Accuracy of Automated Tests", Journal of American Academy of Audiology, vol. 18, No. 1, (2007), pp. 78-89.

Margolis, Robert H. et al., "Automated Pure-Tone Audiometry: An Analysis of Capacity, Need, and Benefit", American Journal of Audiology, vol. 17, No. 2, (2008), pp. 109-113.

Smits, Cas et al., "Development and validation of an automatic speech-in-noise screening test by telephone", International Journal of Audiology, vol. 43, No. 1, (2004), pp. 15-28.

Henry, James A. et al., "Comparison of two computer-automated procedures for tinnitus pitch matching", Journal of Rehabilitation Research and Development, vol. 38, No. 5, (2001), pp. 557-566.

Henry, James A. et al., "Computer-automated clinical technique for tinnitus quantification", American Journal of Audiology, vol. 9, No. 1, 36, (2000), Abstract, 1 page.

Henry, James A. et al., "Comparison of manual and computer-automated procedures for tinnitus pitch-matching", Journal of Rehabilitation Research and Development, vol. 41, No. 2, (2004), pp. 121-138.

European Supplementary Search Report of EPO Application No. EP11814110, mailed Jan. 2, 2014, 7 pages.

International Search Report of PCT Application No. PCT/CN2014/070394, mailed Apr. 22, 2014, 5 pages.

International Search Report of PCT Application No. PCT/CN2014/070407, mailed Mar. 27, 2014, 3 pages.

* cited by examiner

METHOD AND SYSTEM FOR SELF-MANAGED SOUND ENHANCEMENT

CROSS-REFERENCES TO RELATED APPLICATIONS

This application contains subject matter related to provisional application Ser. No. 61/371,068 filed Aug. 5, 2010 and Ser. No. 61/379,237 filed Sep. 1, 2010 in the name of inventors of the present invention and assigned to the present assignees.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND

This invention is directed in general to the field of audiology and digital sound engineering and in particular to a system and method for enhancing user experience based on an individualized audiological profile.

Hearing loss has been estimated to be the most prevalent disability in developed countries. Literally millions of people worldwide suffer from hearing disabilities, many of whom are unaware of their hearing loss. The decreased hearing capability may be due to several factors, including age, health, occupation, injury and disease. The loss of hearing can lead to significant reductions in quality of life, impaired relationships, reduced access to employment and diminished productivity. Different types of hearing loss and related conditions can affect people's daily activities in different ways, in particular having phone conversations and listening to music.

In general, hearing sensitivity to high-pitched sound tends to lessen first. People generally are not aware of the decrease in their hearing sensitivities until they experience hearing problems, for instance, difficulty understanding a conversation on the phone or having problems hearing in a noisy environment. For people with hearing deterioration, their hearing capabilities are generally sufficient for most listening situations. Since the impact of their hearing loss is tolerable, they tend to ignore or find a way around it. They might avoid talking on the phone in noisy environments and would unlikely seek help from a hearing healthcare professional.

Individuals with significant hearing loss may consult a hearing healthcare professional to be prescribed and procure a hearing aid. Although wearing a hearing aid is considered as one of the less intrusive assistive technologies for hearing loss patients, it is not without problems. To use a hearing aid during a phone conversation or music enjoyment via headphones is clumsy and inconvenient. People using a hearing aid often experience feedback, the squeal created by hearing aid sound pickup by the hearing aid microphone.

A common problem associated with hearing loss is tinnitus. Tinnitus is a conscious experience of sound that originates in the head (i.e., without an external acoustic source) and may be manifest by an evident audible ringing that interferes with other sounds around one or more frequencies. Tinnitus is a common condition and a symptom normally observed with age-related hearing loss. Tinnitus is known to affect individuals to varying degrees and in a great number of different ways. Some people with chronic tinnitus are able to ignore the condition while others find it annoying, intrusive, distracting, and even disabling. Tinnitus may interfere with sleep, causing both emotional distress and other ill-effects on general health.

Many tinnitus sufferers notice their tinnitus changes in different acoustic surroundings, it is more bothersome in silence and less annoying in sound-enriched environments. This phenomenon has led to the development of sound therapies for tinnitus treatment. The most common recommendation is to "avoid silence" by enriching the background sounds. This can be accomplished by simply playing some background sound or music. More sophisticated sound therapies involve measuring the pitch and loudness of the tinnitus signals and providing signals which can be played via ear level devices and sound generators.

One of the aspects of the present invention is hearing profiling, particularly through self-administered testing. During hearing profiling, minimum audible hearing levels for a set of audiometric frequencies are measured. Various methods are known for obtaining minimum audible hearing levels. During application of hearing profiling to a hearing enhancement device (such as a hearing aid, sound amplifier, personal listening device, such as a smart phone or the like) in a specific situation, however, a person at times may insist on increasing or decreasing device volume in order to sufficiently hear and comprehend otherwise enhanced audio as determined by hearing tests and corresponding modification of the hearing profile at the ear as part of the sound enhancement process. One problem is the unintentional induced loudness in the enhanced audio may cause hearing discomfort and damage. A person may have a higher tolerance level for a certain audiometric frequency while having a lower tolerance level for another frequency. A person's sound loudness tolerance profile differs from person to person. The difference may not be very significant among the people with normal hearing. However, it is not the case for people with various degrees of hearing impairments, such as, hearing loss, tinnitus, and hearing loss with tinnitus. Due to the difference in people's sound loudness tolerance profiles, the hearing curve of a person with normal hearing should not be used as the standard. Thus, fitting of a person's hearing curve without taking into consideration of the person's sound loudness tolerance profile may lead to hearing discomfort or damage.

Simply increasing device volume in order to sufficiently hear and comprehend enhanced audio as governed by the sound enhancement process may be dangerous. Increasing or decreasing device volume implies amplifying or de-amplifying audio of all audiometric frequencies by the same factor. A person typically requires amplifying or de-amplifying a limited range of audiometric frequencies. Increasing or decreasing the loudness of audio of all audiometric frequencies may lead to a range of hearing problems. A system capable of handling the various sound loudness tolerance profiles with various degrees of hearing impairments is needed. More specifically, solutions to the problems identified herein, such as, hearing difficulties during phone conversations, while listening to music, as well as, feedback created by use of a hearing aid, are needed.

Several patents that may be of interest in comparison to the present invention are U.S. Pat. Nos. 7,613,314; 7,529,545; and 6,944,474.

SUMMARY

According to the invention, a system and method are provided for producing a typically normal hearing experience in a hearing impaired individual. Specifically, the present invention includes capturing a person's audio hearing characteristics to produce an individualized audiological profile; analyzing the individualized audiological profile; producing a processed result; and then automatically enhancing the output signals from an audio reproduction apparatus to provide the individual with a processed result as a satisfactory audio experience. The processed result includes individual hearing parameters of frequency-based loudness enhancement and other hearing-related characteristics to address and complement an individual's hearing needs. It accomplishes this activity as closely as possible to a normal hearing standard while maintaining a margin of safety to protect against excessive loudness that may cause discomfort or further hearing damage. The individual user may self-administer a hearing test using a personal device, such as, a smartphone. The individualized audiological profile typically contains the following: (1) measurements at typically three loudness levels (namely the most comfortable, the uncomfortable, and the minimum audible level) at each audiometric frequency; (2) measurements from a tinnitus test, with tinnitus loudness and pitch; and (3) a user's customization settings. Customization settings may include those settings appropriate for or chosen by the user to be implemented in a noisy environment. The invention is useful for any individual seeking an enhanced hearing experience, whether having hearing within normal range or hearing that is impaired. Thus the system is useful as a hearing aid.

In a specific embodiment, the separate functions of the invention may be incorporated into a single multifunction device or multiple devices. A software-based system may be implemented according to the invention on any computerized apparatus, such as, a personal computer, a smart phone, personal amplifier or combination thereof with local, removable, or remote storage of an individualized audiological profile. The software-based system performs a variety of functions. It captures frequency-specific personal audio hearing characteristics and analyzes the characteristics to generate an individualized audiological profile. This profile is stored either locally or remotely and later used as control input to enhance audio from an appropriately programmable audio reproduction apparatus, such as the personal computer, smart phone, personal amplifier or combination thereof, through which audio program or like source material (prerecorded music, for example) is reproduced. At the audio reproduction apparatus, the signal processing comprises receiving audio program material in the form of audio signals in the time-domain; capturing and analyzing the current frequency composition of the acoustic environment to produce therefrom a current environment profile reflecting the ambient sound environment that is updated as the acoustic environment changes; applying the stored individualized audiological profile and the current environment profile to the audio program material through a set of filters, such as finite impulse response digital filters, to calculate a set of desired gains at pre-selected frequencies; modifying the audio program material; converting the modified audio program material from the time domain to the frequency domain; analyzing the loudness tolerance level for the modified audio program material by comparing the levels with the person's sound loudness tolerance level (hereinafter also uncomfortable loudness level—UCL) at each audiological frequency; adjusting the loudness at selected frequencies where the individual's UCL is exceeded to produce a frequency domain audio signal; converting the frequency domain audio signal to its equivalent time domain audio output signal; and conveying the time-domain audio output signal to the individual. The audio hearing characteristics may be stored locally or remotely, and the analysis of the hearing characteristics and processing to produce the individualized audiological profile may be performed and stored locally on a personal device, or it may be stored remotely at a central hearing processing center connected through telecommunication links such as the Internet, and retrieved as needed for reproduction of sound according to the principles of the invention.

In various embodiments of the invention, the principles of the invention may be applied to audio programs in the presence of environmental sources such as white or colored noise, in the presence of a tinnitus condition or both.

Tinnitus can be mitigated in accordance with the present invention. Tinnitus loudness refers to the sensational level (SL) of an individual's tinnitus as calculated by subtracting the minimum audible level of tinnitus pitch from the intensity of the individual's tinnitus. While different approaches may be used to address tinnitus, one approach is through the use of sound therapy. Tinnitus relieving signals are generated according to the tinnitus pitch and loudness that have been measured when capturing the audio hearing characteristics that are used to form the individualized audiological profile. These generated relieving signals are used independently (without other enhancement) or embedded as part of the reproduced sound.

The invention allows any user of a computerized apparatus to readily produce an individualized audiological profile to complement the individual's personal needs while providing a safety margin against discomfort and hearing damage, with the goal of bringing the user's hearing experience back to "normal." In addition, self-administered as well as professionally administered and other audio hearing characteristics test results can be captured, analyzed, and stored locally and/or remotely. While the normal hearing experience is achieved automatically, users may optionally be provided with the capability of modification of the established normal hearing experience according to their liking.

The invention recognizes the significant gap between hearing test results and sound enhancement processes and provides a bridge between the two. The hearing characteristics analyzed according to a proven methodology are the dictating factors of the sound enhancement process resulting in a normal hearing experience.

The invention will be more clearly understood by reference to the following detailed description in connection with the accompanying drawings.

DESCRIPTION OF SPECIFIC EMBODIMENTS

Figure 1A:
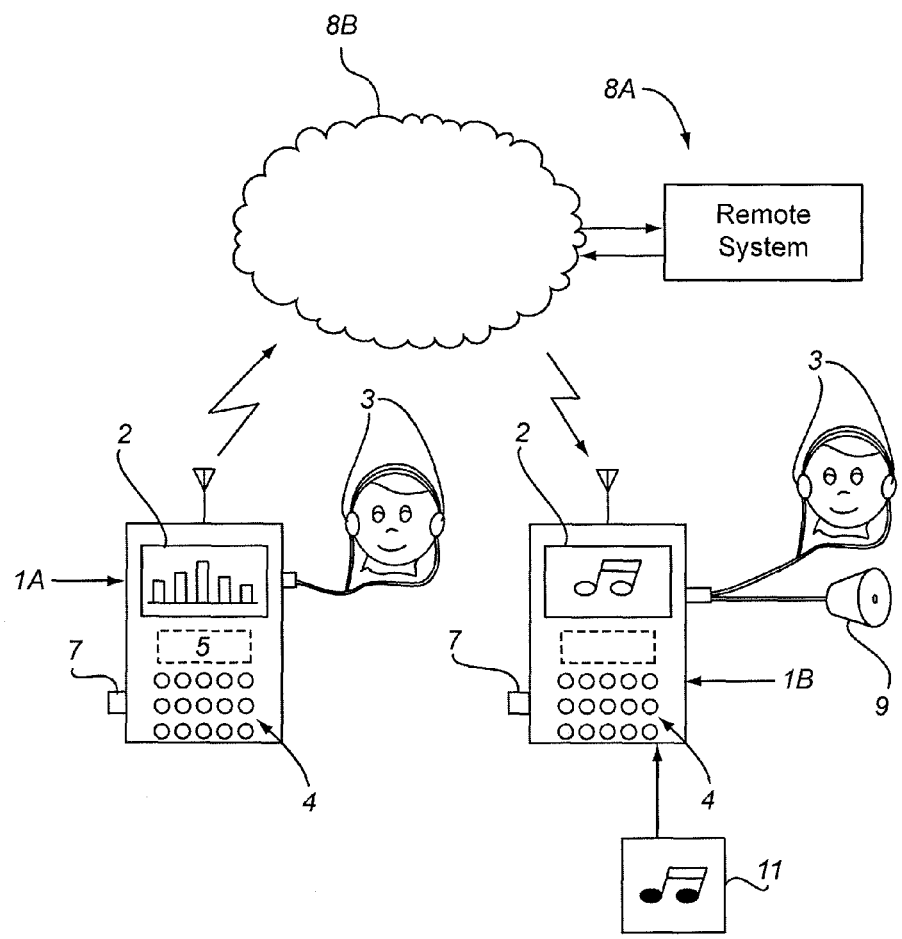
FIG. 1A is a high-level block diagram illustrating uses of one or more personal devices in connection with a remote storage medium in accordance with the invention.

Referring to FIG. 1A, a high level block diagram of a personal device 1 is shown with representative environmental elements. The device 1A has a display 2, a set of earphones 3 and a control interface 4, such as a keyboard. The device 1A stores or receives a test regimen 5 that is activated by its individual user via the control interface 4, which then interacts with the hearing of the user who responds as hereinafter explained. An individualized audiological profile as hereinafter explained is generated which is stored locally in the device 1A, or on a removable storage device (thumb drive or nonvolatile memory card) 7 or remotely in a remote analysis and storage system 8A accessible via telecommunication links 8B. The individualized audiological profile is used on the same or similar device 1B to modify its audio signal output to the same earphones 3 or to a loudspeaker 9. The audio signal output is based on input of programming material 11 whose frequency-dependent and time-dependent characteristics are regulated by the individualized audiological profile and an environment profile developed from the current environment as hereinafter explained.

Figure 1B:
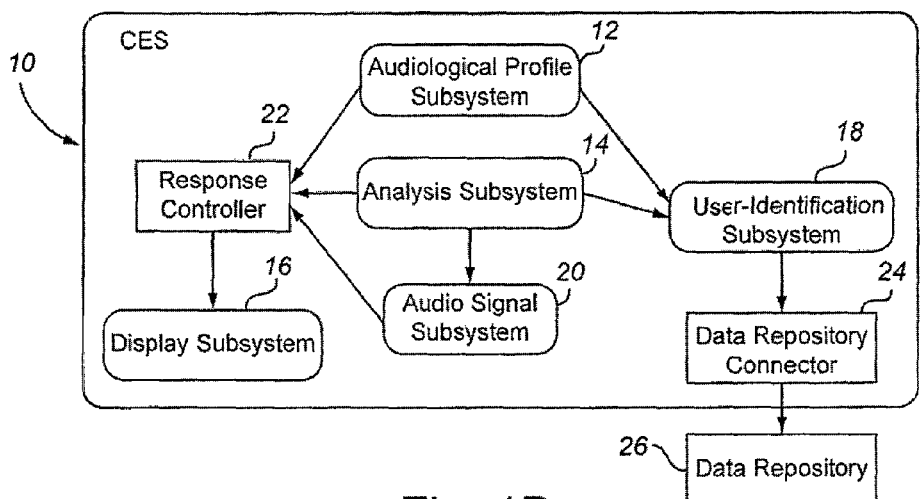
FIG. 1B is a high-level block diagram of a system according to the invention.

Referring to FIG. 1B, to implement the invention, a Customized Enhanced Sound™ (CES) system 10 is provided having subsystems and classes for information input, audiological profiling, analysis, display, user identification, response control, and data repository. A class as used herein is a description of a software-based group of objects with similar properties, common behaviors, common relationships, and common semantics. A subsystem is a set of classes collaborating to fulfill behavior(s) for which the subsystem is responsible. Each class plays a role in the subsystem by handling different responsibilities and communicating with each other to fulfill each responsibility.

Implemented in software on a general purpose hardware platform of appropriate capabilities, the system 10 of device or devices 1A/1B/8A provides the dual functions of testing to develop profiles and of sound reproduction in a particular environment. In the testing mode, the system 10 interactively measures personal hearing capabilities in one function (typically prior to use for subsequent storage) and measures environmental sound/noise in another function (typically contemporaneous with reproduction). The system 10 stores the individualized audiological profile locally or remotely. The system 10 stores the environment profile locally. Analysis of raw data to generate the individualized audiological profile may also be performed either locally or remotely (via telecommunication links). In the reproduction or playback mode, the system 10 modifies a source audio program (input audio signals) according to the individual and environment profiles to adapt the program to the hearing capabilities and preferences of the individual user. In a specific embodiment, the system 10 captures and measures, or receives captured data, analyzes the data, generates target gain for each audiometric frequency, applies the target gain and/or tinnitus relieving signals to the audio signal, and forms the enhanced audio output signals with safeguards against uncomfortable or damaging loudness.

Components of the CES system 10 include an audiological profile subsystem 12, analysis subsystem 14, display subsystem 16, user-identification subsystem 18, audio signal subsystem 20, response controller 22, and data repository connector 24 in communication with a data repository 26 (which can be local or remote).

Audiological Profile Subsystem

The audiological profile subsystem 12 conducts tests performed separately on each ear, as related to the user's audio hearing characteristics. The subsystem responsibilities include: determining a user's hearing characteristics; determining a user's tinnitus characteristics; determining a user's most comfortable loudness level for each audiometric frequency; determining a user's uncomfortable loudness level for each audiometric frequency; generating audio test signals on demand; determining the user's audio hearing characteristics from a professionally administered hearing test; and generating the individualized audiological profile.

Figure 2:
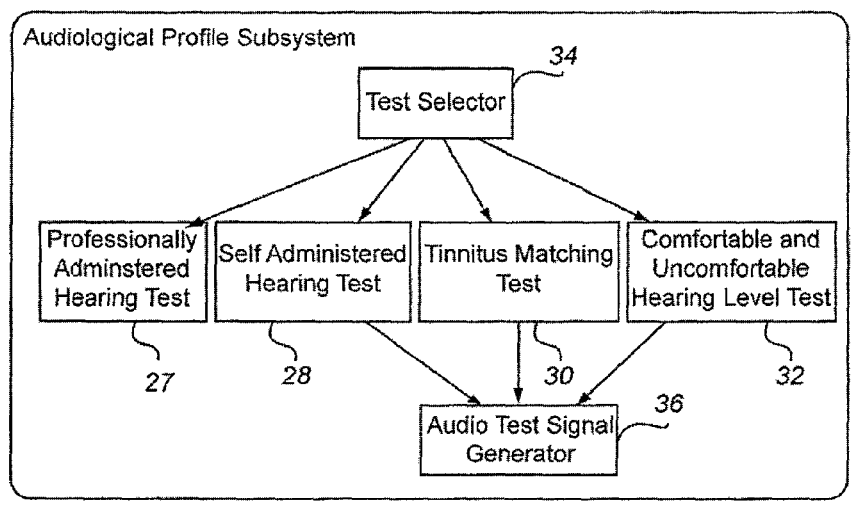
FIG. 2 is a high-level block diagram of an audiological profile subsystem.

Referring to FIG. 2, the classes in the audiological profile subsystem include: a professionally administered hearing test class 27; a self-administered hearing test class 28; a tinnitus matching test class 30; a Comfortable and Uncomfortable hearing level test class 32; a test selector 34; and an audio test signal generator class 36.

Analysis Subsystem

The analysis subsystem 14 analyzes the user's individualized audiological profile and produces a processed result which is used by the audio signal subsystem for the generation of the enhanced audio output signals. The subsystem responsibilities include interpreting the user's audiological profile; determining needed audio gains; determining the type or types of relieving sounds to generate; generating the specified relieving sound; and handling the user's customization settings. The types of relieving sounds supported are: a) music, b) narrow-band noise, c) broadband noise, d) environmental sound, and e) pure tone audio signals.

Figure 3:
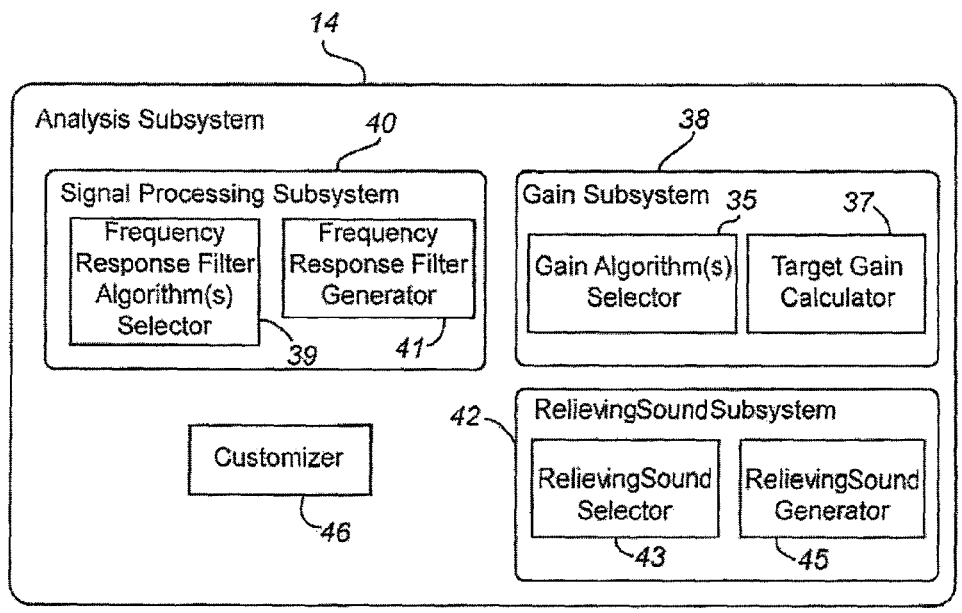
FIG. 3 is a block diagram of an analysis subsystem according to the invention.

Referring to FIG. 3, the subsystems and classes of the analysis subsystem 14 include: gain subsystem 38, signal processing subsystem 40, relieving sound subsystem 42, and customizer class 46. Within the gain subsystem 38 the classes are a gain algorithm selector 35 and a target gain calculator 37. Within the signal processing subsystem 40 the classes are an algorithm selector 39 and a filter generator 41. Within the relieving sound subsystem 42 the classes are a relieving sound selector 43 and a relieving sound generator 45.

User-Identification Subsystem

Figure 4:
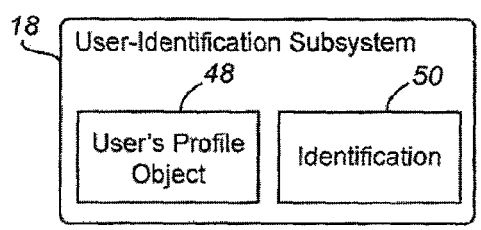
FIG. 4 is a block diagram of a user-identification subsystem.

The user-identification subsystem 18 manages the user identification process and maintains individualized audiological profiles. The subsystem 18 responsibilities include determining the identity of the user; verifying the identity of the user; and maintaining the user's individualized audiological profile. Referring to FIG. 4, the classes in the user-identification subsystem 18 include the profile object 48 and identification of the user 50.

Audio Signal Subsystem

Figure 5:
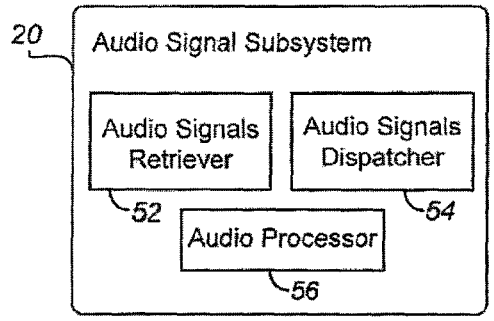
FIG. 5 is a block diagram of an audio signal subsystem.

The audio signal subsystem 20 manages all issues related to the storage and utilization of audio signals. The subsystem responsibilities include: retrieving pre-enhanced audio signals from an audio programming source; generating from the pre-enhanced audio signals the enhanced audio signals based upon the processed result from the analysis subsystem; and dispatching the enhanced audio signals. Referring to FIG. 5, the classes in the audio signal subsystem 20 include an audio signals retriever 52, audio signals dispatcher 54, and audio processor 56.

Display Subsystem

The display subsystem 16 provides all the user interface elements that the user interacts with when using the present invention and may be of conventional design appropriate to the system 10.

Data Repository Connector

The data repository connector 24 is a class that manages the connection with the data repository 26. The class responsibilities include: establishing a database connection; generating a database query statement(s); retrieving/updating/inserting/deleting data into and from the data repository 26; and retrieving data from the data repository 26.

Response Controller

The response controller 22 is a module that interprets what needs to be displayed based upon on the requests. Its responsibilities include determining and sending the necessary information to be displayed to the display subsystem.

Logical Flow of Framework

Figure 6A:
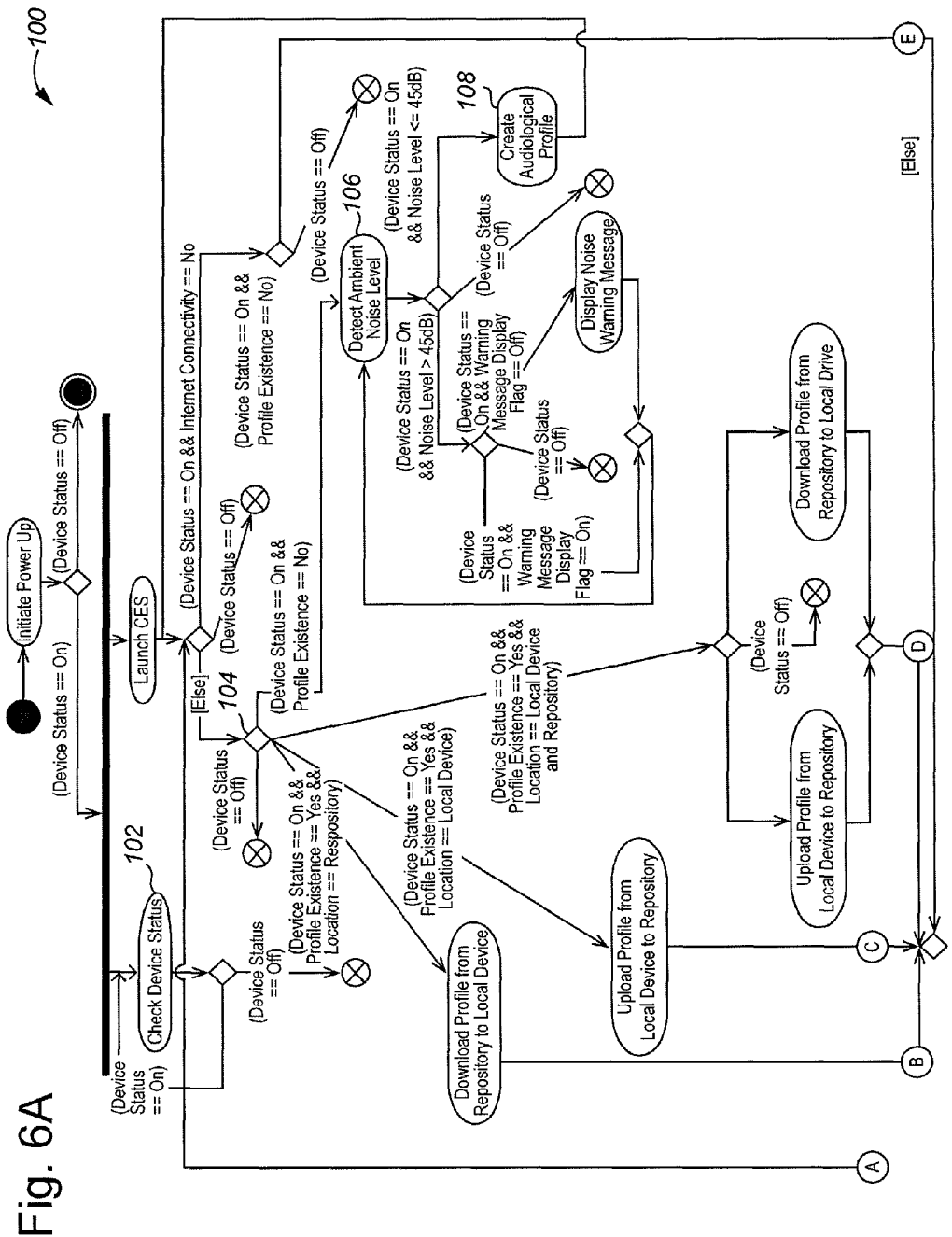
FIGS. 6A and 6B are together an activity diagram of a sound enhancement process according to the invention.
Figure 6B:
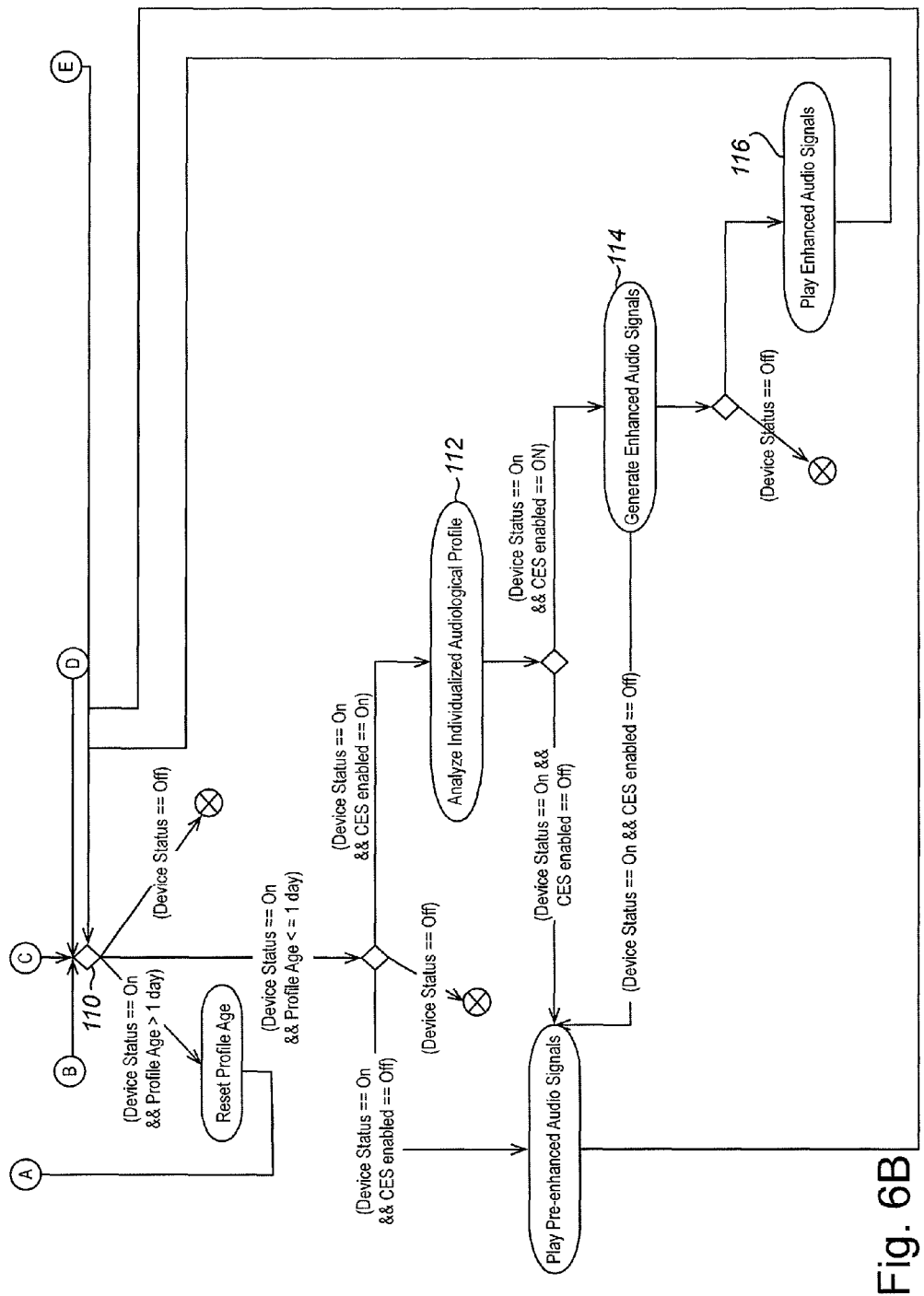

FIGS. 6A and 6B and the following paragraphs describe the logical flow of the CES system 10 and process 100 according to the present invention in an activity diagram. The activity diagram of the software-based system shown in FIGS. 6A and 6B is largely self-explanatory and includes the nodes, basic functionality and interrelationships of elements in the sound enhancement process. The sound enhancement process includes: monitoring user device status 102; determining whether a user profile exists and location in which the profile is stored 104; detecting the ambient noise level 106; generating an individualized audiological profile 108; determining the date and time of the user profile; analyzing individualized audiological profile 112; generating the enhanced audio signals 114; and playing enhanced audio of the enhanced audio signals on a user device 116. For several of the major steps of the sound enhancement process, there are several example embodiments provided in outline (pseudo-code) form as follows:

Monitor User Device Status (Check Device Status)
Check for the existence of device's power signal
If there exists power signal,
   Mark the device status to ON.
If there exists no power signal,
   Mark the device status to OFF.
\*\* The software-based system performs device status monitoring constantly and in parallel with the other processes within the sound enhancement process. At any given point in time, if the device status equals to OFF, the software-based system will stop functioning.

Check for Profile Existence and Location in which the Profile is Stored
   Check for Internet connectivity
   If there exists no Internet connectivity and the device status equals to ON
     Check for profile existence
       If the local device has a profile,
         Check for profile age
       If the local device has no profile the device status equals to ON,
         Detect ambient noise level and generate audiological profile
   If there exists Internet connectivity and the device status equals to ON,
     Check for profile existence and location of the profile
       If the data repository has the profile and the device status equals to ON,
         Download the profile from the data repository to local device
         Check for profile age and signal enhancement
       If the local device has the profile and the device status equals to ON,
         Upload profile from local device to data repository
         Check for profile age and signal enhancement
       If both the data repository and the local device have the profile and the device status equals to ON,
         Compare the time stamp of the two profiles
           If the local profile is the most recent and device status equals to ON,
           Upload profile from local device to data repository
           Check for profile age and signal enhancement
           If the profile in the data repository is the most recent and the device status equals to ON,
           Download profile from data repository to local device
           Check for profile age and signal enhancement
       If no profile is found and the device status equals to ON,
         Detect ambient noise level, then generate audiological profile
Check for Profile Age and Signal Enhancement
If the profile age is greater than one day old and the device status equals to ON,
Reset the profile age
   Check for profile existence and location in which the profile is stored
If the profile age is less than or equals to one day old and the device status equals to ON,
   Check for CES status
     If CES has been enabled,
       Analyze individualized audiological profile
         Generate enhanced audio signals
           Play enhanced audio
     If CES has been disabled,
       Play pre-enhanced audio
Detect ambient noise level (Environment)
Measure the level of the ambient noise
If the ambient noise level is greater than 45 dB and the device status equals to ON
   Display warning message
     Detect ambient noise level
If the ambient noise level is less than or equals to 45 dB and the device status equals to ON
   Create individualized audiological profile
The environment profile is updated continually real time during playback of audio program material. A typical cycle for updating the environment profile is 100 ms. However, updating can occur more or less frequently from a digitized sound sample rate of about 16 ms to 50 ms to several minutes in slow-changing ambient noise environments.

Figure 7:
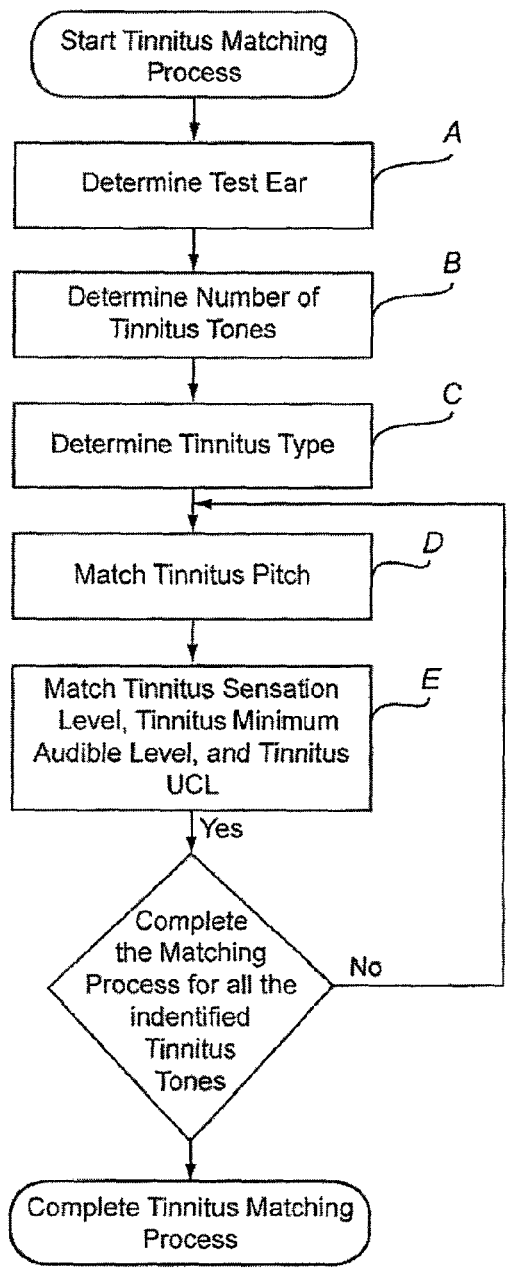
FIG. 7 is a flow chart of the tinnitus matching process.

Generate Individualized Audiological Profile
Select the type of hearing test to perform
If the user selects a self-administered hearing test
    Perform pure tone audiometry for each ear separately
        Play an audio signal at each audiometric frequency
        Ask the user to select the minimal audible level at each audiometric frequency
        Repeat the pure tone audiometry until the minimal audible level for all audiometric frequencies have been captured
    Perform uncomfortable hearing test for each ear separately
        Play an audio signal at each audiometric frequency
        Ask the user to select the uncomfortable loudness level at each audiometric frequency
        Repeat the uncomfortable hearing test until the uncomfortable loudness level for all audiometric frequencies have been captured
    Perform the most comfortable hearing test for each ear separately
        Play an audio signal at each audiometric frequency
        Ask the user to select the minimum audible level at each audiometric frequency
        Repeat the pure tone audiometry until the minimum audible level for all audiometric frequencies have been captured
    Request user's willingness to perform tinnitus matching test
        If the user wants to perform tinnitus matching test
            Perform tinnitus matching test
                Determine the test ear
                Determine tinnitus type
                Match the tinnitus pitch
                Match the tinnitus loudness
        If the user does not want to perform tinnitus matching test
            Skip the tinnitus matching test
If the user selects professionally administered hearing test
    Enter the air conduction unmasked minimum audible level for all audiometric frequencies for each ear
    Enter the air conduction masked minimum audible level for all audiometric frequencies for each ear
    Enter the bone conduction unmasked minimum audible level for all audiometric frequencies for each ear
    Enter the bone conduction masked minimum audible level for all audiometric frequencies for each ear
    Enter the bone conduction forehead unmasked minimum audible level for all audiometric frequencies
    Enter the bone conduction forehead masked minimum audible level for all audiometric frequencies for each ear
    Enter the uncomfortable loudness level for all audiometric frequencies for each ear
    Enter the most comfortable loudness level for all audiometric frequencies for each ear
    Enter tinnitus matching result
    Enter the result from the speech reception threshold test
    Enter the result from the speech discrimination test
    Enter the audio source used in the speech reception threshold test
    Enter the audio source used in the speech discrimination test Create the individualized audiological profile from the captured data As noted above, one regimen of tests is for hearing sensitivity at various frequencies, and another regimen of tests is for individual tinnitus. The tinnitus pitch, tinnitus sensation level, tinnitus minimum audible level and tinnitus UCL test regimen is a process termed the tinnitus matching process. The type of tinnitus considered by this invention is: subjective, namely the perception of sounds without any external sound sources. The regimen is carried out in five steps. Referring to FIG. 7, the steps are: test ear determination (A); tinnitus tone number determination (B); tinnitus type determination (C); tinnitus pitch determination (D); and tinnitus sensation level determination (E). These steps are explained below in greater detail.

Step 1: Test Ear Determination

Figure 8:
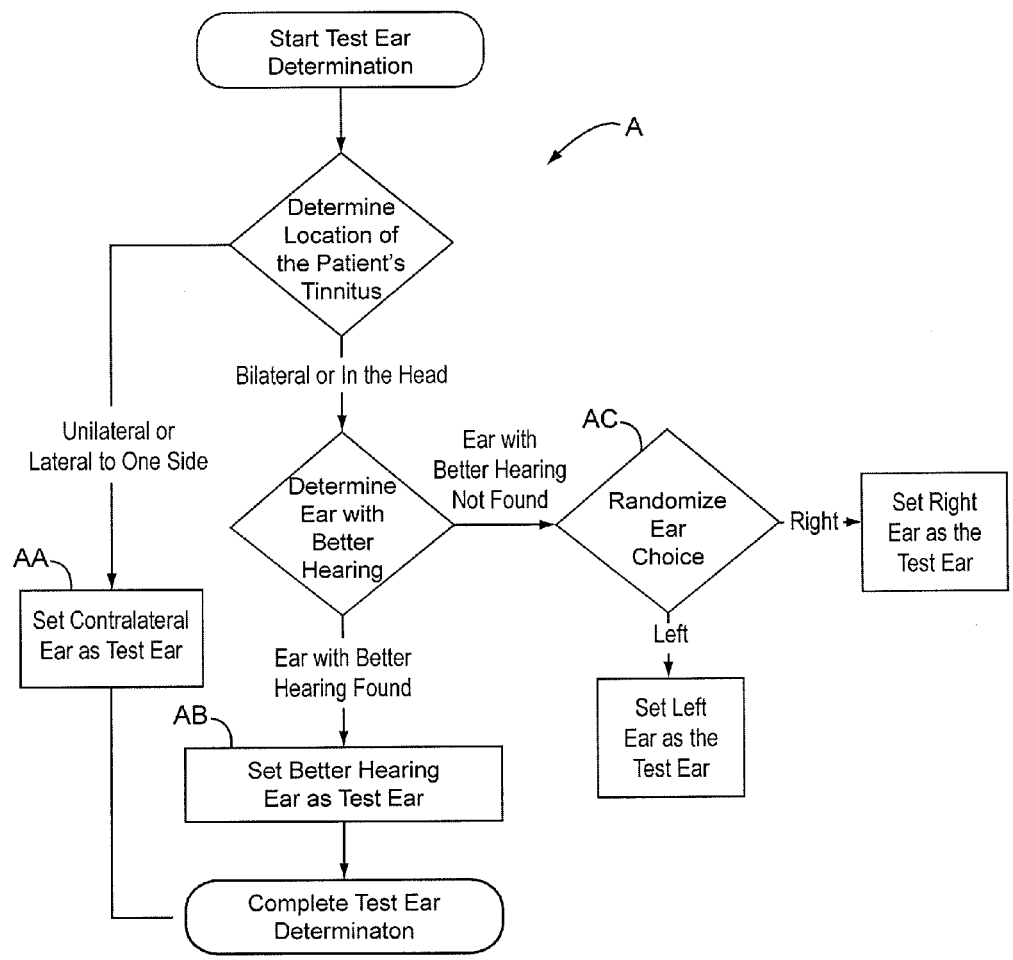
FIG. 8 is a flow chart of the test ear selection process of the tinnitus matching process.

The purpose of this step is to determine which ear to use as the test ear. A user can perceive tinnitus at various locations: unilateral, bilateral, and head. Depending on the reported location of the tinnitus, the test ear would be selected accordingly. FIG. 8 outlines the procedure involved and is largely self-explanatory. The following points relate to specific steps.

If the reported location of the perceived tinnitus is unilateral, the contralateral ear would be considered as the test ear (AA). The choice of using the contralateral ear is to minimize the possible interference between tinnitus and test stimuli and to increase the accuracy of the test result.

If the reported location of the perceived tinnitus is lateral to one side, the contralateral ear would be considered as the test ear (AA). The choice of using the contralateral ear is to minimize the possible interference between tinnitus and test stimuli and to increase the accuracy of the test result.

If the reported location of the perceived tinnitus is in neither unilateral nor lateral to one side of the individual's head, the ear with better hearing would be considered as the test ear (AB). In the case where there is no difference in the hearing ability between two ears, the test ear would be chosen randomly (AC).

Step 2: Number of Tinnitus Tones Determination

Figure 9:
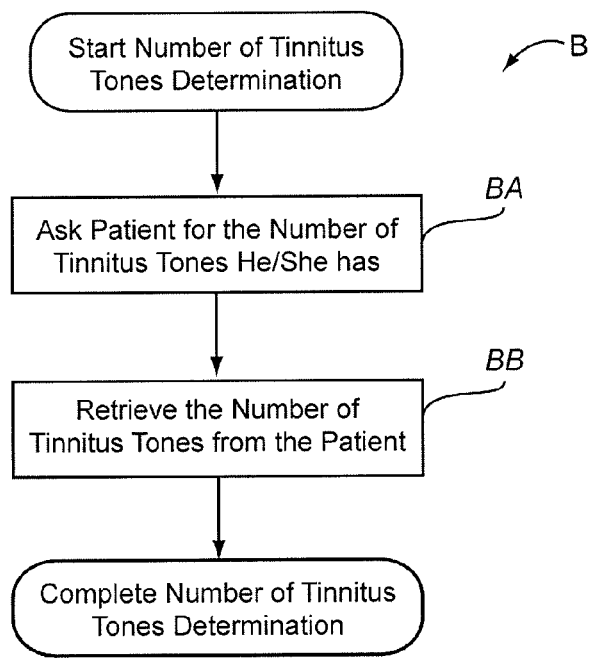
FIG. 9 is a flow chart of the tone number determination test of the tinnitus matching process.

Tinnitus is perceived as tonal. The purpose of this step is to determine the number of tinnitus tones the user perceives. Referring to FIG. 9, the determination process would request the user for the number of tinnitus tones the user has and saves the inputted value (BA). In one embodiment of this invention, the test focuses on the most troublesome tinnitus tone (often a personal, subjective determination by the individual). In another embodiment, the test focuses on the two most significant tinnitus tones. Yet, in another embodiment, the test and its profiling supports any number of tinnitus tones in which case all such tones would be noted (BB).

Step 3: Tinnitus Type Determination

Figure 10:
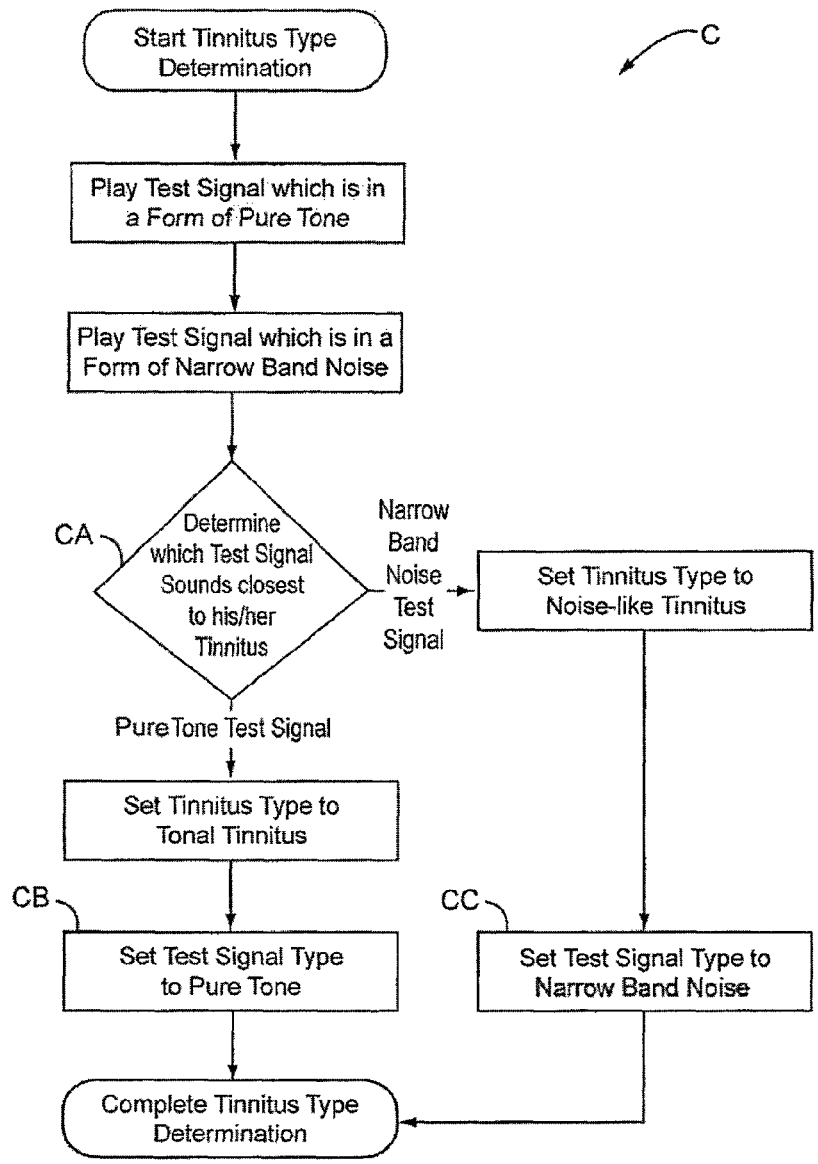
FIG. 10 is a flow chart of the tinnitus type determination process of the tinnitus matching process.

The purpose of this step is to determine the type of tinnitus (tonal tinnitus or noise-like tinnitus). FIG. 10 illustrates this step. The procedure sets the test signal type accordingly (CA). If the user has tonal tinnitus, the test signal type will be in a form of pure tone (CB). If the user has noise-like tinnitus, the test signal type will be in a form of narrow-band noise (CC).

In one embodiment of this invention, the determination process begins by playing two test signals at 4000 Hz to a user, one in a form of pure tone and the other in a form of narrow band noise. The choice of playing the test signals at 4000 Hz is because most people report having tinnitus in the range of 4000 Hz. The user is requested to compare the test signals and select the one which sounds closest to their tinnitus. From the user's choice in test signal, the type of tinnitus will be derived and the test signal type is set accordingly.

Step 4: Tinnitus Pitch Determination

The purpose of this step is to measure the user's perceived tinnitus pitch. The determination process would play test signals for a range of audiometric frequencies. Each test signal is played at 10 dB SL, meaning 10 dB above the pre-measured minimum response level for the corresponding frequency. The user would select the one that sounds closest to the user's own tinnitus pitch.

In one embodiment of this invention, the user is required to repeat the Tinnitus Pitch Determination three times and the final matched tinnitus pitch would be the average of those measurements. If the user has more than one tinnitus tone, the user would have to perform the Tinnitus Pitch Determination six times, three for each tinnitus tone.

Various methods may be used for measuring tinnitus pitch. In one embodiment of this invention, the discrete-frequencies method is used. The set of test signals will be in a form of discrete data. The determination process, using a two alternative forced-choice approach, presents pairs of test signals and the user would choose the one that is closest in pitch to the user's tinnitus.

Figure 11:
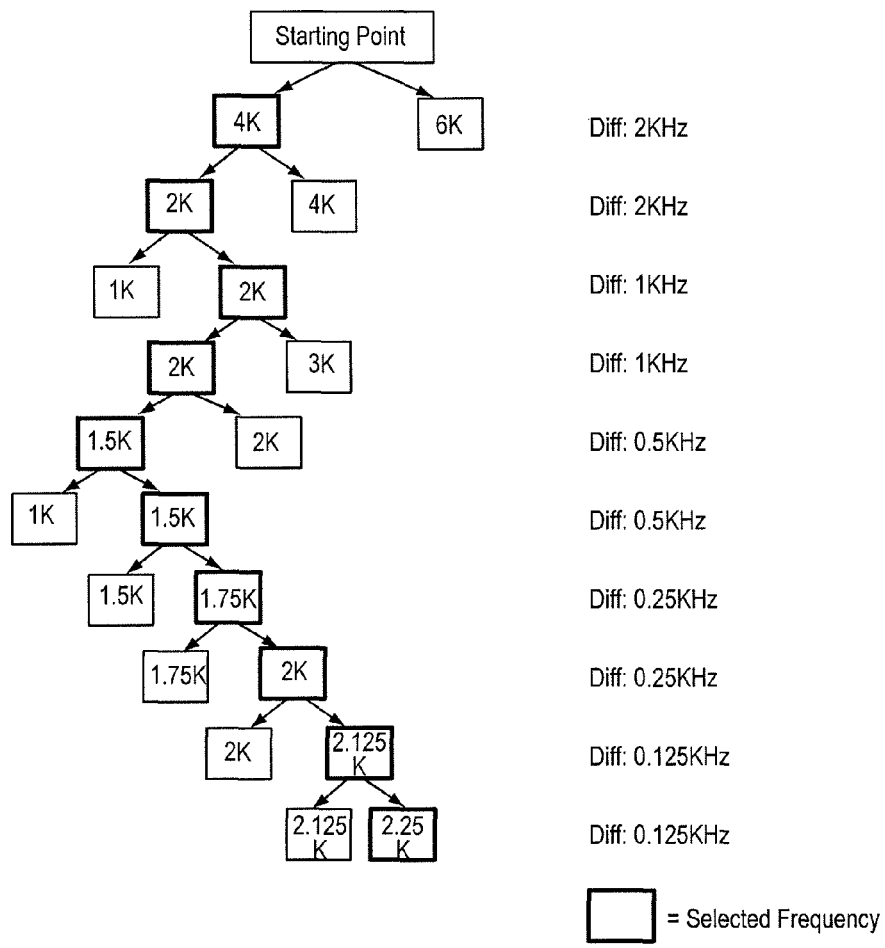
FIG. 11 is a diagram of the test signal tone to tinnitus tone selection process of the tinnitus matching process.
Figure 12:
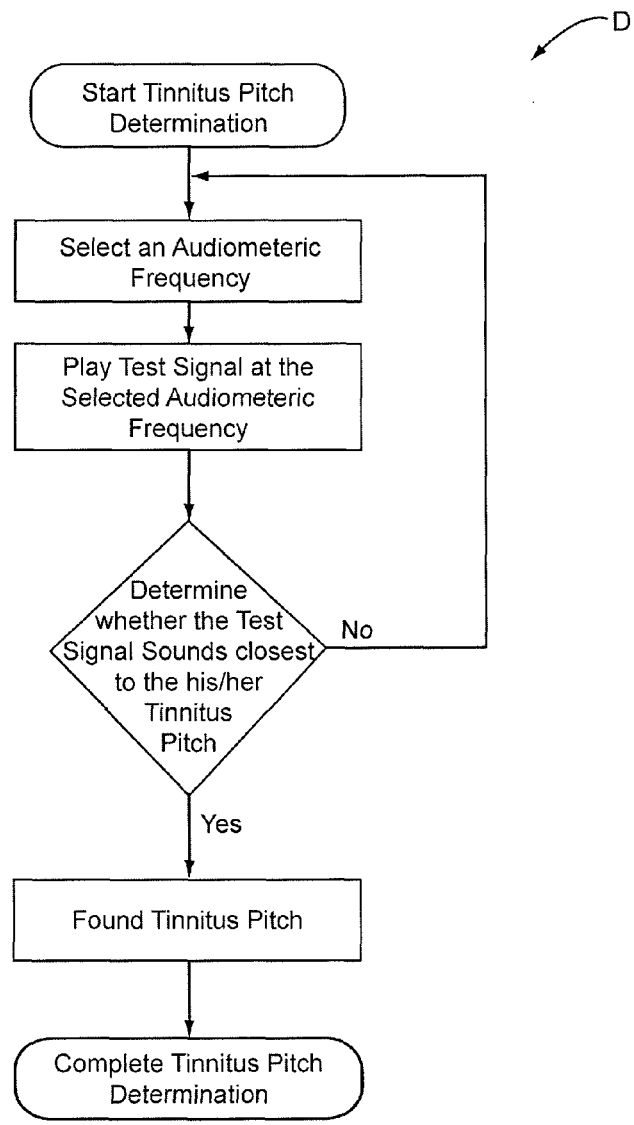
FIG. 12 is a flow chart of the tinnitus pitch determination process of the tinnitus matching process.
Figure 13A:
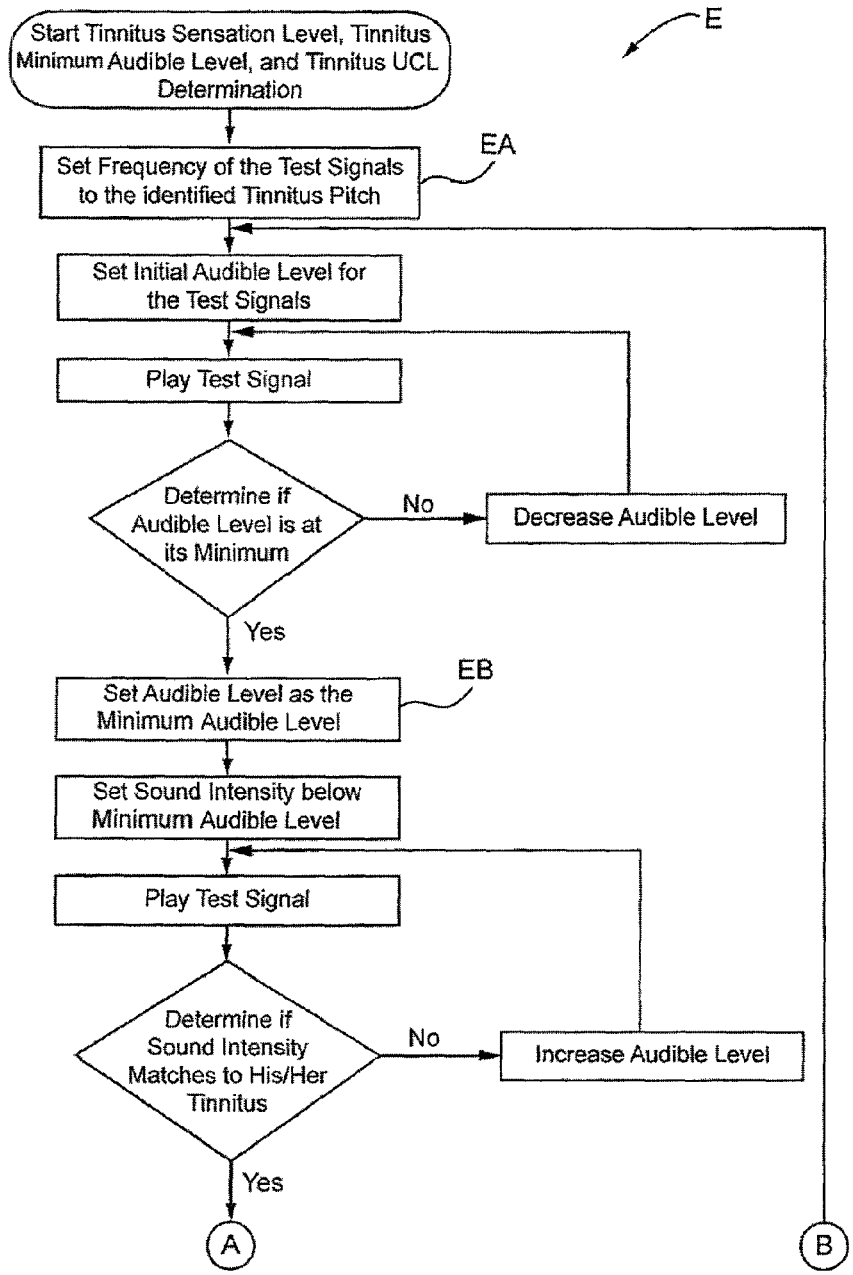
FIGS. 13A and 13B are together a flow chart of the three-level tinnitus test for each tinnitus pitch of the tinnitus matching process.
Figure 13B:
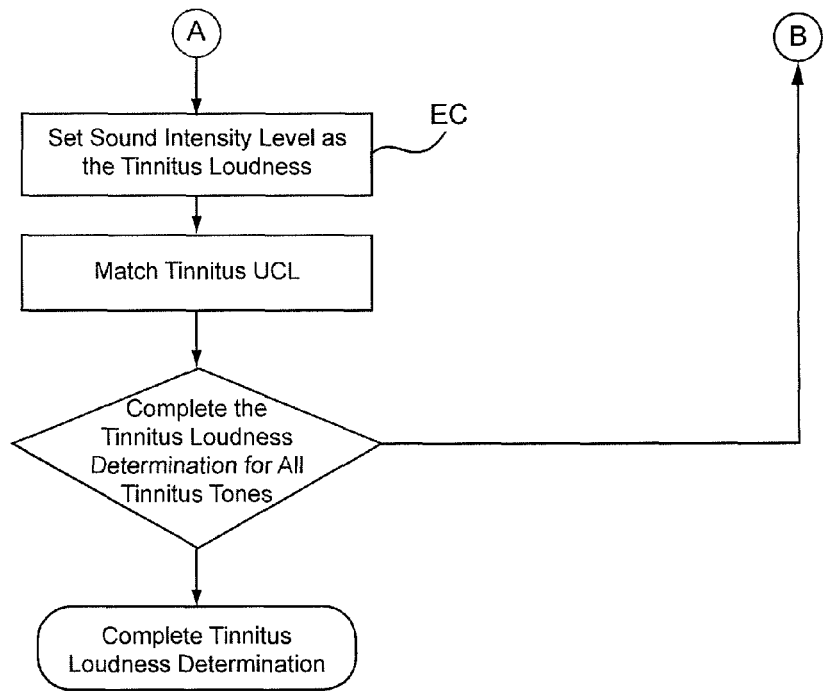

FIG. 11 is one example of the tinnitus determination process. The determination process begins at 4000 Hz. This is chosen because most users report to have their tinnitus at approximately 4000 Hz. The test completion criterion is to obtain an accuracy of 125 Hz for all frequencies. In another embodiment of this invention, the continuous-frequencies method is used. Referring to FIG. 12, the set of test signals may take on values within a finite interval of frequencies. The user picks the one that is close in pitch to the user's tinnitus Step 5: Tinnitus Sensation Level, Tinnitus minimum Audible Level, and Tinnitus Uncomfortable Loudness Level Determination The tests of the three levels of minimum sensation, comfortable and UCL are applied to each tinnitus tone. To the extent the general three-level test may require illustration; the flow chart of FIGS. 13A and 13B is exemplary. In the multiple-characteristic test illustrated in FIGS. 13A and 13B, the determination begins by setting the frequency of test signals to the identified tinnitus pitch (EA). The next task is to identify the minimum audible level at the tinnitus pitch (EB). The determination process plays test signals at various audible levels and the user is asked to identify the one which the user considers as the minimum audible level. This is an iterative process. Then, the test is to identify the sensation level of their tinnitus. During the determination process test signals are played at various audible levels starting at the level below the minimum audible level. The user is asked to identify the test signal which is equal in loudness to the user's tinnitus. At this point the sound intensity is set as the Tinnitus Loudness (EC). The Tinnitus Sensation Level is calculated by subtracting the Tinnitus Minimum Audible Level (EB) from the Tinnitus Loudness (EC).

In one embodiment, the tinnitus uncomfortable loudness level (TUCL) is captured by playing a narrow band noise of an identified tinnitus pitch to the user and requests the user to identify the level at which the loudness of the noise causes discomfort. In another embodiment, the user is required to repeat the Tinnitus Sensation Level and Tinnitus Minimum Audible Level Determination three times. The final matched sensation level will be the average of those measurements. If the user has more than one tinnitus tone, they may be required to undergo the determination process.

The individualized audiological profile, including the results of analysis of the tinnitus tests, is obtained prior to sound reproduction, i.e., the sound enhancement process. This profile may be updated on any scheduled basis, but it is typically updated on a daily basis to ensure the sound enhancement process is current.

Figure 14:
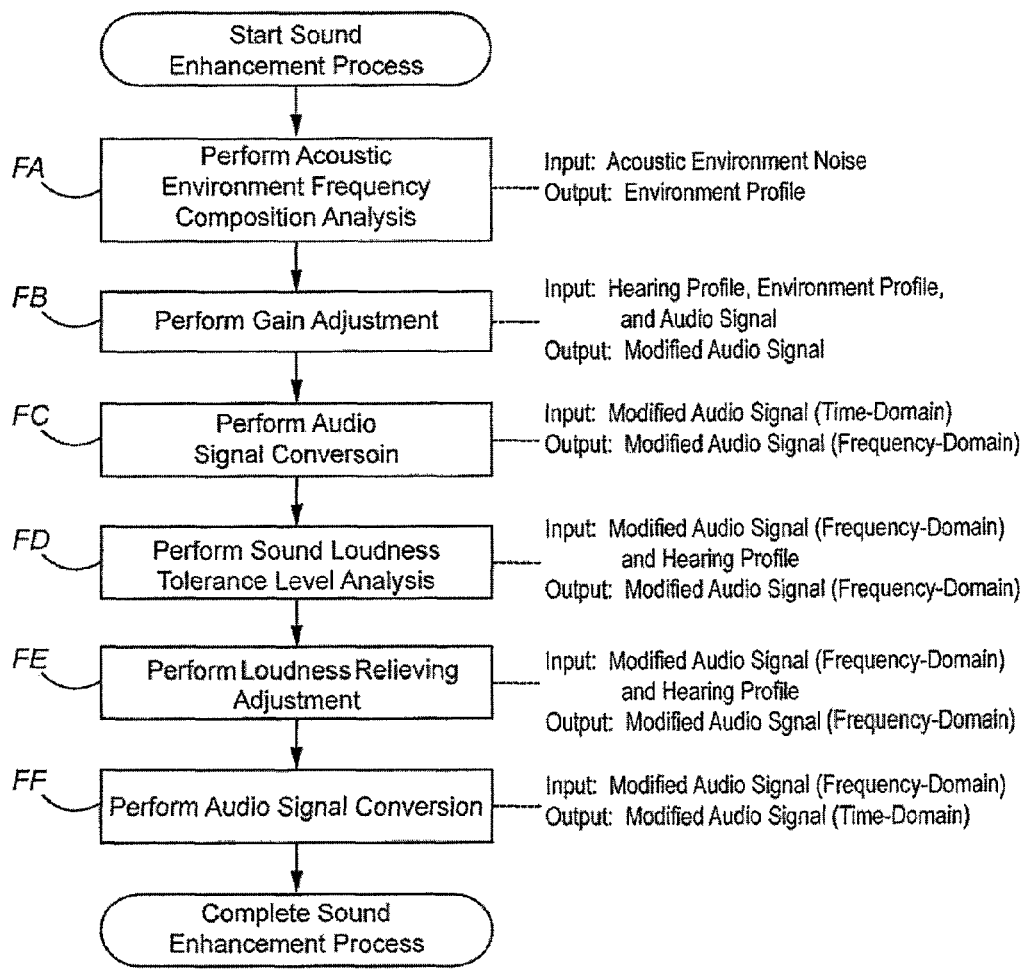
FIG. 14 is a flow chart of the sound enhancement process.
Figure 15:
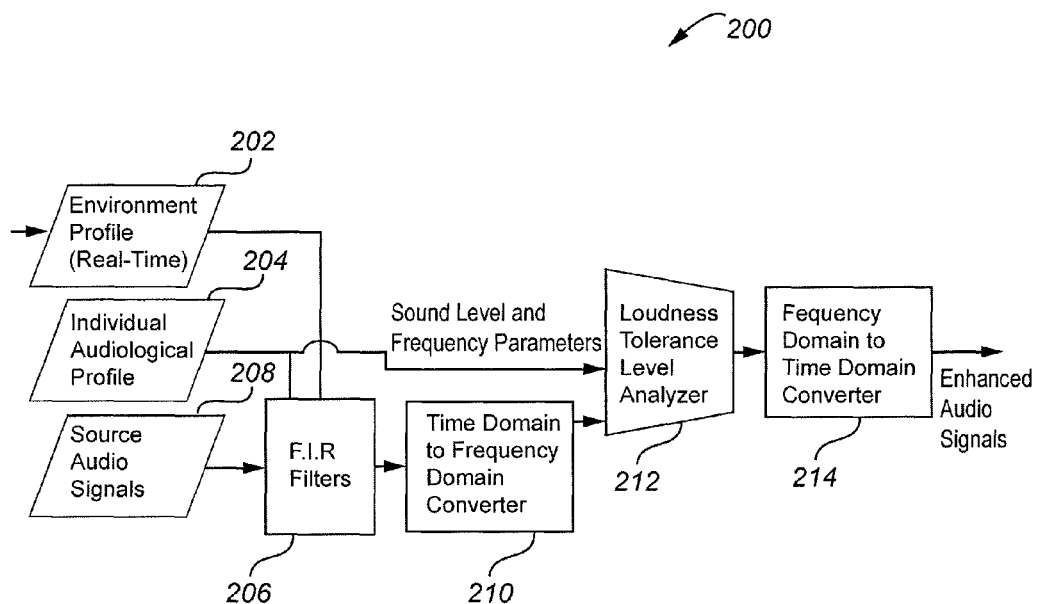
FIG. 15 is a high level block diagram of a device having the capabilities of the process of FIG. 14.

The sound enhancement process of the present invention is broadly summarized in FIG. 14. It depicts the processing of audio program material as an audio signal in conjunction with the individualized audiological profile 204 and preferably the latest, i.e., current, environment profile 202 as further depicted in FIG. 15. The sound enhancement process begins with an acoustic environment frequency composition analysis (FA). The system automatically captures and analyzes the frequency composition of the acoustic environment. As described above, it then generates the environment profile 202. The system provides the stored individualized audiological profile 204 comprising the minimum audible levels, sound loudness tolerance levels, and current environment profile, along with an audio signal to be adjusted for gain (FB). The environment profile and the individualized audiological profile are used to derive the coefficients or parameters for a filter(s), such as finite impulse response (FIR) filter(s) 206. The filter(s) are used to provide desired frequency-specific gains which are determined based upon the individualized audiological profile and audio signals 208 of the audio program material from any source. They are applied through the filter(s) which modify the passed-in audio signal accordingly. With a modified audio signal generated, the system converts it from a time-domain representation to a frequency-domain audio signal through a Fourier analyzer 210 (FC). Thereafter, the frequency domain representation is applied through a sound loudness tolerance level analyzer 212 where sound loudness tolerance level analysis takes place (FD). The sound loudness tolerance level analysis involves examining the loudness of the modified audio signal and comparing it with the user's sound loudness tolerance level at each audiometric frequency in accordance with the stored individualized audiological profile. If the loudness level at a specific frequency is greater than the user's sound loudness tolerance level, the system will adjust the loudness accordingly (FE). With the completion of the tolerance level analysis, the system converts the adjusted frequency-domain audio signal back to its equivalent time-domain audio signal in an inverse Fourier transform module 214 (FF) to produce the desired enhanced audio signals to be played as enhanced audio. Any loudness caution signal provided to the user can then be released.

In one embodiment of this invention, the system 10 refers to the uncomfortable loudness level as the sound loudness tolerance level, and to hearing loss as the type of hearing impairment being considered.

In another embodiment of this invention, the system 10 further refers to tinnitus pitch, tinnitus sensation level, tinnitus minimum audible level, and tinnitus UCL as the sound loudness tolerance level and hearing loss with tinnitus as the type of hearing impairment being considered.

The system 10 provides both automatic and manual gain adjustment options to the user where the automatic gain adjustment option is triggered by the acoustic environment and the manual gain adjustment option is user triggered.

In one embodiment of the present invention, the system 10 begins to function with initiating the acoustic environment frequency composition analysis. The system automatically captures and analyzes the frequency composition in the current acoustic environment and creates an updated environment profile on a scheduled basis, oftentimes at every 50 ms. The system then uses the updated environment profile characteristics to automatically determine the amount of gain needed to allow the user to comfortably hear as desired and comprehend the enhanced audio without suffering any new or advanced ear damage.

In another embodiment of the present invention, the system 10 provides the user with multiple gain adjustment options. The user may dynamically adjust the amount of gain needed to sufficiently hear and comprehend enhanced audio as governed by the sound enhancement process in various circumstances.

In summary, this software-based system automates the enhancement process of audio from a computerized apparatus to complement a user's unique audio hearing characteristics based upon the user's individualized audiological profile. The individualized audiological profile can be obtained through either a self-administered hearing test or a professionally administered hearing test. The self-administered hearing test refers to profiles created from a computerized apparatus. This approach performs a capturing process on each ear and includes taking a hearing test, a UCL test, a most comfort level (MCL) test and/or a tinnitus matching test. Not all of these tests are necessary to use the system 10 and are considered optional. The system saves the individualized audiological profile on the local hearing enhancement apparatus and/or submits a copy to a data repository. The professionally administered test refers to profiles compiled from data provided by an appropriate healthcare professional. As outlined below, the data from a professionally administered test includes a pure tone audiogram, UCL and MCL test results for each audiometric frequency and tinnitus characteristic. The healthcare professional may enter the data on a suitably enabled apparatus or through the Internet into the web-accessed data repository.

A software-based system according to the invention will have the capability to accept any parameters from a professionally produced audiogram. Such parameters include, according to standard designations in the art: Among the conventional tests are AC Unmasked or Masked, BC Unmasked or Masked, BC Forehead Unmasked or Masked, PTA, MCL, UCL, SRT Speech Discrimination, and Audio Source used in the Speech Reception Threshold (SRT) and Speech Discrimination Tests, i.e., sound clips on CD or tape, or computer generated sound clips for both the left and right ears at the following frequencies:

Hearing Level in dB at 125 Hz
Hearing Level in dB at 250 Hz
Hearing Level in dB at 500 Hz
Hearing Level in dB at 1 kHz
Hearing Level in dB at 2 kHz
Hearing Level in dB at 3 kHz
Hearing Level in dB at 4 kHz
Hearing Level in dB at 6 kHz
Hearing Level in dB at 8 kHz By default, the system bases its sound enhancement process on the most recent individualized audiological profile. During operation, the system compares the most recent individualized audiological profile to those on the local apparatus and the data repository. If the one stored in on the data repository 26 is more current, it will overwrite the local version (unless otherwise configured). If the profile on the local apparatus is more current, the system uploads the local profile to the data repository. In the absence of Internet connectivity, the system will use the local profile for the sound enhancement process. The date and time comparison process is typically performed daily with frequent monitoring for profile changes on the local apparatus. Whenever the system detects changes, it recalculates the gains and performs the sound enhancement with the updated data.

Referring to the following paragraphs, a sample implementation of Custom Enhanced Sound (CESound), also known as the ACEHearing process, according to$_{[BKL1]}$ the invention is presented as a series of pseudo-code listings. To enhance clarity of this pseudo-code, there is no attempt at succinctness through use of language-specific statements that are common in certain programming languages, such as, Java. The intent here is to employ generic statements whose interpretation will be obvious to those of normal skill in software programming.

```
enable CESound(Boolean enable) {
/**
 * If the user is turning CESound off, then disable all filters
 */
    if (enable == false) {
    disableAllFilters( );
    return;
    }
    /**
    * If the user is turning CESound on, then perform the following:
    * - get the user's audiological profile
    * - calculate the proper filter coefficients based on the current
    algorithm
    * - generate input filters (for use with the capturing device(s),
    such as microphone or sound card input
    * - generate the output filters (for use with the output device(s),
    such as the speaker or headphone)
    * - apply the input filters to the capturing device(s)
    * - apply the output filters to the output device(s)
    */
    UserProfile userProfile = getUserProfile( );
    FilterCoefficients filterCoefficients =
    calculateFilterCoefficients(userProfile);
    Array inputFilters = generateInputFilters(filterCoefficients);
    Array outputFilters = generateOutputFilters(filterCoefficients);
    applyFilters(inputSource, inputFilters);
    applyFilters(outputDevice, outputFilters);
UserProfile get UserProfile( ) {
UserProfile userProfile = new UserProfile( ); // the UserProfile object
to be returned
/*
* If able to connect to the central database at the remote data repository,
then synch with it to ascertain whether we have the most current active
user profile for the user
*/
if (connectToCentralDatabase( ) = true) {
User user = getCurrentUser( );
userProfile = syncUserProfile(user);
} else {
/*
* If unable to connect to the central database, then use the
* latest active user profile in the local database on the device
*/
userProfile = getLocalUserProfile( );
}
return userProfile;
}
perform HearingTest( ) {
UserProfile userProfile = new UserProfile( );
performMinimalAudibleLevelTest(userProfile);
performMostUncomfortableLevelTest(userProfile);
if (modelDialogAsk("Would you like to perform Tinnitus Matching?")) {
performTinnitusMatchingTest(userProfile);
}
acquireUserInformation( );
saveToLocalDatabase(userProfile);
saveToCentralDatabase(userProfile);
}
perform MimimalAudibleLevelTest(UserProfile userProfile){
userProfile.setMALRight1000(RIGHT_EAR,1000);
userProfile.setMALRight2000(RIGHT_EAR,2000);
userProfile.setMALRight4000(RIGHT_EAR,4000);
userProfile.setMALRight8000(RIGHT_EAR,8000);
userProfile.setMALRight250(RIGHT_EAR,250);
userProfile.setMALRight500(RIGHT_EAR,500);
userProfile.setMALLeft1000(LEFT_EAR,1000);
userProfile.setMALLeft2000(LEFT_EAR,2000);
```

-continued

```
userProfile.setMALLeft4000(LEFT_EAR,4000);
userProfile.setMALLeft8000(LEFT_EAR,8000);
userProfile.setMALLeft250(LEFT_EAR,250);
userProfile.setMALLeft500(LEFT_EAR,500);
perform MostUncomforableLevelTest(UserProfile userProfile){
userProfile.setMALRight1000(RIGHT_EAR,1000);
userProfile.setMALRight2000(RIGHT_EAR,2000);
userProfile.setMALRight4000(RIGHT_EAR,4000);
userProfile.setMALRight8000(RIGHT_EAR,8000);
userProfile.setMALRight250(RIGHT_EAR,250);
userProfile.setMALRight500(RIGHT_EAR,500);
userProfile.setMALLeft1000(LEFT_EAR,1000);
userProfile.setMALLeft2000(LEFT_EAR,2000);
userProfile.setMALLeft4000(LEFT_EAR,4000);
userProfile.setMALLeft8000(LEFT_EAR,8000);
userProfile.setMALLeft250(LEFT_EAR,250);
userProfile.setMALLeft500(LEFT_EAR,500)
"int saveToCentralDatabase(userProfile userProfile) {
if (openConnectionToCentralDatabase( ) == false){
   return CONNECTION_FAILED;
   }
int returnCode= updateProfileToCentralDatabase(userProfile);
closeConnectionToCentralDatabase( );
return returnCode;
}"
performTinnitus MatchingTest(UserProfile userProfile){
userProfile.set TinnitusMatchingFrequency(get TinnitusMatching
Frequency);
userProfile.set TinnitusMatchingAmplitude(get TinnitusMatching
Amplitude);
}
```

The invention has been explained with reference to specific embodiments. Other embodiments will be evident to those of ordinary skill in the art. Therefore, it is not intended that the invention be limited, except as indicated by the appended claims.

What is claimed is:

1. A system for enhancing an individual's hearing experience comprising:
a component for capturing and storing audio hearing characteristics of the individual;
a component for analyzing the individual's audio hearing characteristics and tinnitus characteristics of the individual to generate an individualized audiological profile;
a component for applying said individualized audiological profile to provide an enhanced audio signal to the individual;
a component for generating an environment profile for use to adapt the enhanced audio signal to the ambient sound environment and
a component for performing a tinnitus test, the tinnitus characteristics of the individual including results of a tinnitus test performed on the individual by said tinnitus test component, the results including a tinnitus location, a tinnitus pitch, a tinnitus type selected from tonal tinnitus and tinnitus perceived as noise, a minimum loudness level audible to the individual at the identified tinnitus pitch, a sensation level of the individual's tinnitus, and a tinnitus uncomfortable loudness level of a narrow band of noise at the identified tinnitus pitch.

2. The system according to claim 1, the enhanced audio signal being generated by a computerized apparatus, to compensate for frequency-dependent loudness deficits in the individual's hearing within customized loudness levels.

3. The system according to claim 2, wherein the applying component is an audio amplification element of a personal hearing aid device.

4. The system according to claim 1, wherein the applying component is an audio amplification element of a personal hearing aid device.

5. The system of claim 1, further comprising a component for generating and providing to the individual a tinnitus relieving sound corresponding to the individual's tinnitus characteristics, the relieving sound being selected from the group consisting of music, narrow-band noise, broadband noise, environmental sound, and pure tone audio signals.

6. The system of claim 5, configured to provide sound to the individual including said tinnitus relieving sound embedded in enhanced audio produced by the applying component applying said individualized audiological profile to transform input audio.

7. A system for enhancing an individual's hearing experience comprising:
a component for capturing and storing audio hearing characteristics of the individual;
a component for performing a tinnitus test;
a component for analyzing the individual's audio hearing characteristics and tinnitus characteristics of the individual, including results from a tinnitus test performed on the individual by said tinnitus test component, the results including a tinnitus location, a tinnitus pitch, a tinnitus type selected from tonal tinnitus and tinnitus perceived as noise, a minimum loudness level audible to the individual at the identified tinnitus pitch, a sensation level of the individual's tinnitus, and a tinnitus uncomfortable loudness level of a narrow band of noise at the identified tinnitus pitch, to generate an individualized audiological profile; and
a component for applying said individualized audiological profile to provide an enhanced audio signal to the individual,
the analyzing component comprising a subsystem programmed to produce a processed result according to gain calculations that are frequency-dependent and listening-environment-dependent, and if the processed result exceeds said tinnitus uncomfortable loudness level of the narrow band of noise at the identified tinnitus pitch, to adjust the processed result to reduce the loudness level at said narrow band of noise to below said tinnitus uncomfortable loudness level.

8. The system according to claim 7, further including a data repository for storing individualized audiological profiles, the repository being configured for collecting data from any source and for storing, updating, and responding to requests for specific individualized audiological profiles for use by the analyzing component.

9. The system according to claim 7, the individualized audiological profile comprising customization settings of the individual.

10. The system according to claim 7, wherein said data repository is configured to include professionally administered hearing test data.

11. The system according to claim 7, wherein said data repository is accessible through an Internet connection.

12. The system according to claim 7 wherein said capturing component is a portable electronic component.

13. The system according to claim 7, wherein said analyzing component is a portable electronic component.

14. A method for providing enhanced audio to an individual, tailored to audiological characteristics of the individual, comprising:
capturing the individual's audio hearing characteristics, including determining a threshold uncomfortable loudness level of the user for at least one frequency and the individual's minimum audible level for at least one audiometric frequency, at least in part by a self-administered test;

generating an environment profile including at least an environmental sound measurement;

analyzing the individual's hearing characteristics to generate an individualized audiological profile;

storing the individualized audiological profile in a storage means;

using the environment profile and the individualized audiological profile to determine a first gain adjustment for an input audio signal to compensate for frequency-dependent loudness deficits in the individual's hearing;

determining a modified audio signal produced by applying the first gain adjustment to an input signal;

periodically determining whether the loudness of the modified audio signal at one or more audiometric frequencies equals or exceeds said threshold uncomfortable loudness level;

applying a second gain adjustment to reduce the loudness of the modified audio signal at frequencies, if any, at which the loudness of the modified audio signal is determined to meet or exceed the threshold uncomfortable loudness level, to produce an enhanced audio signal in which said threshold uncomfortable loudness level is not exceeded, and providing the enhanced audio signal to the individual in the profiled environment using a personal electronic device that reproduces sound.

15. The method according to claim 14, said capturing the individual's audio hearing characteristics further including determining the individual's most comfortable level for at least one audiometric frequency.

16. The method according to claim 14, said capturing the individual's audio hearing characteristics further comprising a tinnitus test component performing a tinnitus test on the individual, the individualized audiological profile further including measurements from the tinnitus test.

17. The method of claim 14, further comprising periodically updating the environment profile during provision of the enhanced audio to the individual.

18. The method of claim 14, wherein said applying the first gain adjustment to determine said modified audio signal is performed in the time domain, further comprising converting said modified audio signal from the time domain to the frequency domain, performing said second gain adjustment on the modified audio signal in the frequency domain to produce said enhanced audio signal in the frequency domain, and converting said enhanced audio signal from the frequency domain to the time domain before said providing the enhanced audio signal to the individual.

19. The method of claim 14, said storage means being remotely located from the personal electronic device, and the method further comprising, before using the individualized audiological profile to determine said first gain adjustment, downloading the individualized audiological profile to the personal electronic device from said storage means via an Internet connection.

20. The method of claim 14, said storage means including remote storage means remotely located from the personal electronic device and local storage means located in the personal electronic device, and the method further comprising, before using the individualized audiological profile to determine said first gain adjustment, the personal electronic device following programmed instructions to:

determine whether a local copy of said profile exists in the local storage means and whether a remote copy of said profile exists in the remote storage means;

if said local profile copy exists but said remote profile copy does not exist, upload said local profile copy to said remote storage means to create said remote profile copy;

if said remote profile copy exists but said local profile copy does not exist, download said remote profile copy to said local storage means to create said local profile copy;

if both said local profile copy and said remote profile copy exist, compare the age of said copies, and if one profile copy is a newer profile copy and the other profile copy is an older profile copy, cause said newer profile copy to be copied from its respective storage means to the storage means of the older profile copy; and if neither said local profile copy nor said remote profile copy exists, initiate said capturing the individual's audio hearing characteristics and said analyzing the individual's hearing characteristics to generate an individualized audiological profile.

21. A system for enhancing an individual's hearing experience comprising:

a component for capturing and storing audio hearing characteristics of the individual, including a minimum audible loudness level and a threshold uncomfortable loudness level for at least one audiometric frequency;

a component for analyzing the individual's audio hearing characteristics to generate an individualized audiological profile;

a component for storing the individualized audiological profile;

a component for accessing said audiological profile from said storing component;

a component for determining from the accessed individualized audiological profile a modified audio signal produced by applying a frequency-specific gain adjustment to an input signal; and a component for determining whether the loudness of the modified audio signal at one or more audiometric frequencies equals or exceeds said threshold uncomfortable loudness level, a component for converting the modified audio signal to an enhanced audio signal having reduced loudness relative to the modified audio signal at frequencies, if any, at which the loudness of the modified audio signal is determined to meet or exceed said threshold uncomfortable loudness level; and a component of a personal electronic device for providing said enhanced audio signal to the individual.

22. The system of claim 21, said storing component being a remote storing component located remotely from the personal electronic device, and said profile accessing component being programmed with instructions to download the individualized audiological profile to the personal electronic device from said remote storing component via an Internet connection.

23. The system of claim 21, said storing component including a local storing component in the personal electronic device and a remote storing component located remotely from the personal electronic device, said profile accessing component being programmed with instructions to:

determine whether a local copy of said profile exists in the local storing component and whether a remote copy of said profile exists in the remote storing component;

if said local profile copy exists but said remote profile copy does not exist, upload said local profile copy to said remote storing component to create said remote profile copy;

if said remote profile copy exists but said local profile copy does not exist, download said remote profile copy to said local storing component to create said local profile copy;

if both said local profile copy and said remote profile copy exist, compare the age of said copies, and if one profile copy is a newer profile copy and the other profile copy is an older profile copy, cause said newer profile copy to be copied from its respective storing component to the storing component of the older profile copy; and if neither said local profile copy nor said remote profile copy exists, initiate said capturing and storing component and said analyzing component to generate said individualized audiological profile.

* * * * *